United States Patent [19]
Weiss et al.

[11] 3,981,561

[45] Sept. 21, 1976

[54] OPTICALLY ACTIVATED EXCIPLEX SHUTTER/ATTENUATOR

[75] Inventors: Joel A. Weiss, Fairfax; James P. Sheridan, Burke, both of Va.

[73] Assignee: The United States of America as represented by the Secretary of the Navy, Washington, D.C.

[22] Filed: Oct. 16, 1975

[21] Appl. No.: 623,144

[52] U.S. Cl. ............................ 350/160 P; 350/312
[51] Int. Cl.² ............................................ G02F 1/36
[58] Field of Search ............ 350/160, 311, 312, 316

[56] References Cited
UNITED STATES PATENTS

| | | | |
|---|---|---|---|
| 3,269,267 | 8/1966 | Collins | 350/160 P |
| 3,756,692 | 9/1973 | Scott | 350/160 P |

*Primary Examiner*—William L. Sikes
*Attorney, Agent, or Firm*—R. S. Sciascia; Philip Schneider; Melvin L. Crane

[57] ABSTRACT

A device which provides rapid attenuation of incident light, the degree of attenuation being proportional to the intensity of the light. This system can be used for eye or device protection in sunlight or other situations in which the illuminating source has a spectral output which includes radiation in the 300–400 nm spectral region. The shutter/attenuator can achieve its maximum extinction in less than 100 psec after being illuminated and returns to maximum transmission within 10 nsec after the light is extinguished.

6 Claims, 1 Drawing Figure

U.S. Patent  Sept. 21, 1976  3,981,561
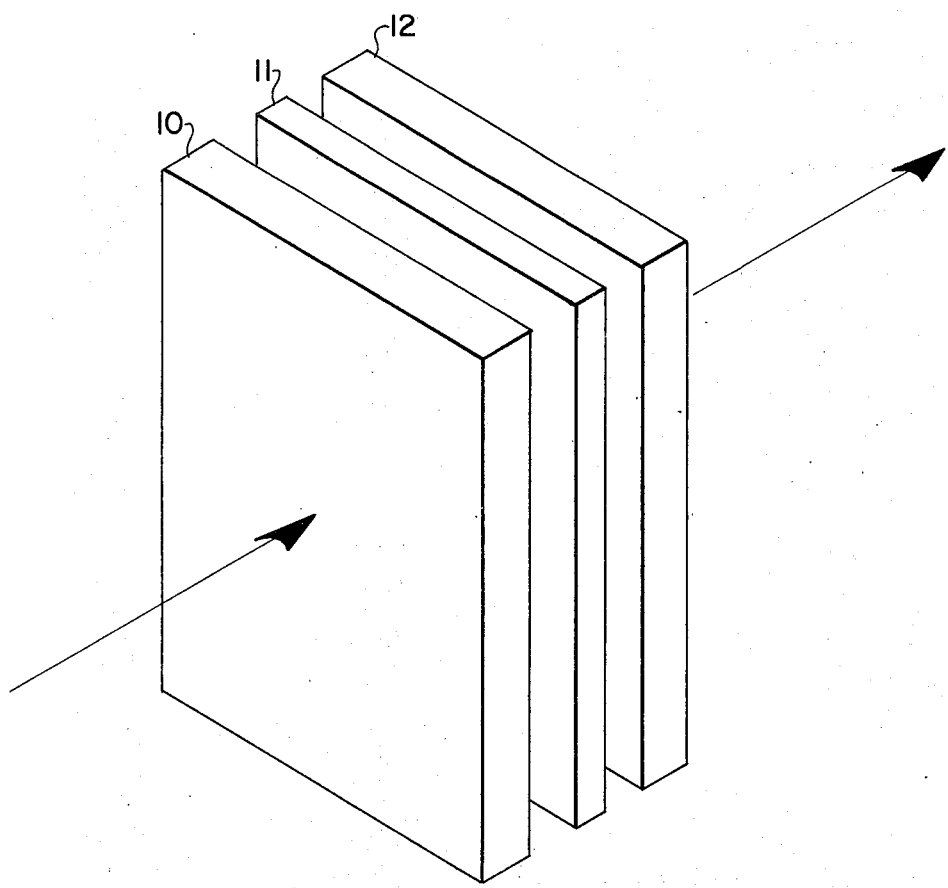

OPTICALLY ACTIVATED EXCIPLEX SHUTTER/ATTENUATOR

BACKGROUND OF THE INVENTION

This invention relates to optically activated radiation intensity control devices and more particularly to such control devices which have a quick response to illuminating radiation and a rapid recovery subsequent to extinction which provides protection against intense fast rising pulses of optical radiation.

Optically activated radiation shutter attenuators have been provided heretofore for protection of the eyes, etc. These devices fall into two categories-passive and active. Passive devices are characterized as those such as sunglasses or other eye protectors which darken due to cross-linking of polymer chains due to exposure to ultraviolet radiation. Such known devices have a relatively long activation and recovery time. Active devices include those electro-optic devices which can be made attenuating with the application of a voltage between electrodes. Such systems require a radiation detector which controls a voltage applied to the electrodes. Voltage on the electrodes then controls the radiation passage characteristics of the optical devices. Such systems usually require high voltages, and often require bulky equipment; however, they can have a time responses of several nsec. Various types of prior art devices are set forth in U.S. Pat. Nos. 3,269,267; 3,370,902; 3,436,144; 3,507,552; and 3,756,692.

SUMMARY OF THE INVENTION

This invention provides protection against intense fast-rising pulses of optical radiation such as encountered in close proximity to an explosive blast. The device makes use of optical elements which permit radiation of a certain wavelength to excite a bi-molecular exciplex solution. The exciplex solution reacts to a range of radiation wavelengths whereas optical elements prevent passage of radiation below and above the operative range of the exciplex solution.

An object of this invention is to provide a passive type device which has a high speed of response to incident radiation and a fast recovery subsequent to radiation incidence.

Another object is to provide a simple long life device for protection of the eyes or instrumentation against optical radiation especially intense fast-rising pulses of optical radiation.

BRIEF DESCRIPTION OF THE DRAWING

The drawing illustrates the relative elements of the device.

DETAILED DESCRIPTION OF THE DRAWING

Now referring to the drawing there is shown by illustration an optically activated optical radiation attenuator which provides rapid attenuation of incident optical radiation and rapid recovery when the incident radiation is removed. The attenuation of incident radiation is proportional to the intensity of the incident radiation. As shown, the device includes an optical radiation transparent box-like cell 10 containing a bi-molecular exciplex solution such as anthracene and diethylaniline.

An exciplex is a charge transfer couplex involving two different materials in solution which exists only after excitation of one of the materials to its first excited electronic level. Bi-molecular exciplexes have been described in a previous publication "Electrode-Transfer and Couplex Formation in the Excited State", by Albert Weller, in *Pure and Applied Chemistry*, No. 16, page 115, 1968.

For species of materials labeled A and B the exciplex reaction is written as $A + B + \lambda\nu_A \rightarrow A^* + B \rightarrow [A^+B^-]$ where the quantity in brackets represents the exciplex which after formation has its own characteristic absorption spectra which is shifted to longer wavelengths than that of either parent species A or B. Most significantly in the absence of exciting radiation the exciplex does not absorb, since it is unstable in the ground state.

The exciplex cell (10) is assembled in combination with an optical radiation filter 11 operative to block radiation below a specific wavelength and to pass all other optical radiation. In order to prevent radiation of an undesired wavelength to pass through the device, an optical radiation filter 12 having a cut-off at a desired longer wavelength is provided. The exciplex cell is positioned for receiving incident radiation and the filter 11 and 12 are positioned for receipt of radiation which has passed through the exciplex cell. Filters 11 and 12 are interchangable and may be placed to either order for the same operation.

In operation of the system for protection of personnel or instrumentation, the system would permit normal radiation to pass through the system. In the event of an intense flash of optical radiation, the exciplex solution will be activated to attenuate the intense incident radiation. In the example cited above using an exciplex of anthracene and diethylaniline, the exciplex cell will be activated by radiation of from about 330–400 nm and absorb radiation up to its maximum absorption of about 800 nm. The low range filter will block all radiation of wavelengths less than 450 nm and the long wavelength filter will block all radiation of wavelengths longer than 800 nm. The exciplex will achieve its maximum extinction in less than 100 psec after being illuminated and will return its maximum transmission within 10 psec after the intense radiation has been extinguished.

It has been determined that a considerable number of exciplex systems may be formed for control of optical radiation of different low and high cutoff wavelengths. For example, a family of exciplexes exist using dicyanoanthracene in combination with a family of aromatic hydrocarbons such as napthalene. Therefore it is seen that by making a suitable choice of the bi-molecular exciplex used and a combination of low and high wavelength filters, specified spectral regions of operation may be formed for protection against intense radiation of a specific wavelength range.

As previously stated, the position in the system of the low and high wavelength filters may be interchanged, however, the exciplex cell must always be first in order to first receive incident radiation. Thus, the exciplex solution is always actuated by the incident radiation prior to passage of the optical radiation to the short and long wavelength cutoff filters.

Obviously many modifications and variations of the present invention are possible in light of the above teachings. It is therefore to be understood that within the scope of the appended claims the invention may be practiced otherwise than as specifically described.

What is claimed and desired to be secured by letters patent of the United States is:

1. An optically activated system for attenuation of incident optical radiation which comprises:
    an optical radiation transparent housing;
    an exciplex solution within said housing;
    a first optical radiation filter for absorbing a desired short wavelength range while passing radiation of longer wavelengths;
    a second optical radiation filter for absorbing optical radiation having wavelength greater than a desired wavelength while passing radiation of a desired wavelength range;
    said housing including said exciplex solution positioned to receive all wavelengths of incident radiation with each of said first and second optical radiation filters positioned to receive radiation passing through said exciplex solution.

2. An optically activated system for rapid attenuation of incident optical radiation as claimed in claim 1; in which
    said exciplex solution is operative for maximum extinction of intense rapid incident radiation in less than 100 psec, and
    recovers to normal upon extinguishment of said radiation in about 10 nsec.

3. A system as claimed in claim 2; in which
    said exciplex solution contains two different species of material each of which have its own characteristic absorption spectra in the absence of incident intense radiation; and
    react together due to incident intense radiation to shift to longer wavelengths than either of said two separate species of material.

4. A system as claimed in claim 3; wherein
    said species of exciplex solution are anthracene and diethylaniline.

5. A system as claimed in claim 3; wherein
    said species of exciplex solution are dicyanoanthracene and an aromatic hydrocarbon.

6. A system as claimed in claim 5; wherein
    said aromatic hydrocarbon consists of napthalene.

* * * * *